United States Patent [19]

Reinehr et al.

[11] Patent Number: 5,545,836
[45] Date of Patent: Aug. 13, 1996

[54] PROCESS FOR THE PREPARATION OF 1,3,5-TRIAZINES

[75] Inventors: Dieter Reinehr, Kandern, Germany; Elek Borsos, Birsfelden, Switzerland

[73] Assignee: Ciba-Geigy Corporation, Tarrytown, N.Y.

[21] Appl. No.: 312,597

[22] Filed: Sep. 27, 1994

[30] Foreign Application Priority Data

Sep. 28, 1993 [CH] Switzerland .................. 2913/93

[51] Int. Cl.⁶ .................................................. C07D 251/24
[52] U.S. Cl. ........................................................ 544/216
[58] Field of Search ................................................ 544/216

[56] References Cited

U.S. PATENT DOCUMENTS

| | | | |
|---|---|---|---|
| 3,113,940 | 12/1963 | Johns et al. | 260/248 |
| 3,113,942 | 12/1963 | Johns et al. | 260/248 |
| 3,294,798 | 12/1966 | Schaefer et al. | 260/248 |
| 3,932,402 | 1/1976 | Norell | 260/248 |
| 5,288,867 | 2/1994 | Reinehr et al. | 544/219 |
| 5,288,868 | 2/1994 | Reinehr et al. | 544/219 |
| 5,298,030 | 3/1994 | Burdeska et al. | 8/442 |

FOREIGN PATENT DOCUMENTS

| | | |
|---|---|---|
| 549969 | 4/1932 | Germany . |
| 480090 | 12/1969 | Switzerland . |
| 1294322 | 10/1925 | United Kingdom . |
| 1518836 | 7/1978 | United Kingdom . |
| WO94/05645 | 3/1994 | WIPO . |

OTHER PUBLICATIONS

Johns et al, J. Org. Chem. 27, 592 (1962).

*Primary Examiner*—John M. Ford
*Attorney, Agent, or Firm*—Michele A. Kovaleski

[57] ABSTRACT

The invention relates to a simple, one-step process for the preparation of triazines of formula

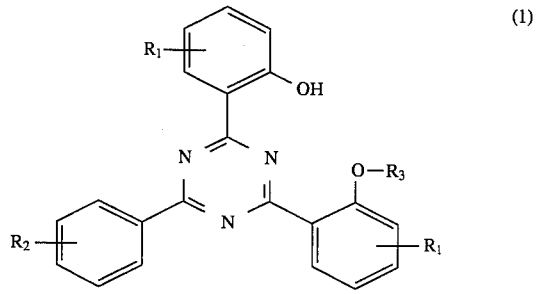

(1)

which comprises reacting the benzonitrile of formula (I)

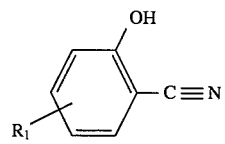

with the benzonitrile of formula (II)

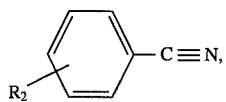

in the temperature range from 180° to 260° C., in which formulae above $R_1$ and $R_2$ are as defined in claim 1.

The compounds prepared by this process find utility as UV absorbers or as starting materials for the preparation of UV absorbers.

10 Claims, No Drawings

PROCESS FOR THE PREPARATION OF 1,3,5-TRIAZINES

The present invention relates to a simple process for the preparation of tris(hydroxyphenyl)-1,3,5-triazines starting from unsubstituted or substituted o-hydroxybenzonitriles and unsubstituted or substituted benzonitriles.

The preparation of symmetrical, tris(hydroxyphenyl)-1,3,5-triazines by trimerisation of aromatic hydroxynitriles is disclosed, inter alia, in U.S. Pat. No. 3,113,942.

The preparation of unsymmetrical substituted triazines by reacting two different nitriles is disclosed in DRP 549969. In this process, the reaction is carried out in the presence of chlorosulfonic acid. The use of hydroxy-substituted arylcyanides for this reaction is not known.

It has now been found that hydroxy-substituted 1,3,5-triazines can be prepared in simple manner starting from unsubstituted or substituted o-hydroxybenzonitriles.

Accordingly, the invention relates to a process for the preparation of triazines of formula

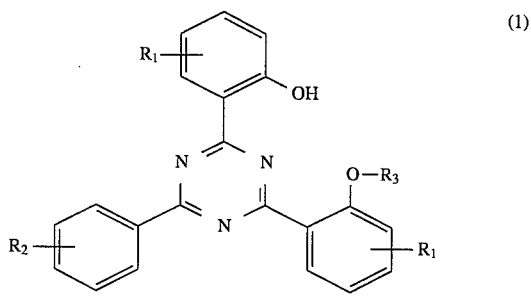

which comprises, in a first reaction step, reacting a benzonitrile of formula (I)

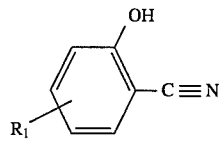

with a nitrile of formula (II)

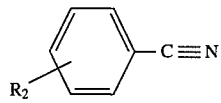

to the compound of formula

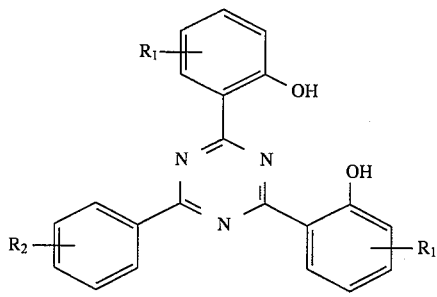

and, in a second reaction step, reacting this compound by selective alkylation to the compound of formula (1), in the temperature range from 180° to 260° C., in which formulae above $R_1$ and $R_2$ are each independently of the other hydrogen, halogen, —C≡N, $C_1$–$C_{18}$alkyl or $C_1$–$C_{18}$alkoxy, and $R_3$ is $C_1$–$C_{18}$alkyl.

$C_1$–$C_{18}$Alkyl and $C_1$–$C_{18}$alkoxy are respectively straight-chain or branched alkyl and alkoxy radicals such as methyl, ethyl, n-propyl, isopropyl, n-butyl, sec-butyl, tert-butyl, amyl, isoamyl or tert-amyl, heptyl, octyl, isooctyl, nonyl, undecyl, dodecyl, tetradecyl, pentadecyl, hexadecyl, heptadecyl or octadecyl, and methoxy, ethoxy, propoxy, butoxy, pentyloxy, hexyloxy, heptyloxy, octyloxy, isooctyloxy, nonyloxy, undecyloxy, dodecyloxy, tetradecyloxy, pentadecyloxy, hexadecyloxy, heptadecyloxy or octadecyloxy.

Halogen is chloro, bromo or iodo. Chloro is preferred.

Suitable alkylation reagents are alkyl halides, dialkyl sulfates, tosylates or dialkyl alkanephosphonates. It is preferred to use dialkyl alkanephosphonates or dimethyl sulfate.

Suitable compounds of formula (1) for the novel process are preferably those in which $R_1$ and $R_2$ are each hydrogen, and $R_3$ is $C_1$–$C_{18}$alkoxy.

The reaction time for the first reaction step is usually 2 to 24 hours, preferably 5 to 12 hours. Solvents and further additives are not necessary for the reaction. The use of catalysts can also be dispensed with.

The preferred reaction temperature is in the range from 180° to 260° C.

The molar ratio of the nitriles of formulae (I) and (II) can vary over a wide range. The preferred molar ratio of the nitriles of formulae (I) and (II) is 2:1 to 1:10.

The first reaction step is usually carried out such that the starting compounds of formulae (II) and (III) are brought together, with stirring, then heated until the reactants are completely fused, and further stirred at this temperature during the indicated reaction time.

The alkylation reaction (second reaction step) is carried out in alkaline medium using sodium or potassium carbonate or dilute sodium or potassium hydroxide solution. In actual practice, the procedure comprises mixing the starting compound, alkali metal carbonate or sodium hydroxide solution together with the alkylating reagent, and stirring the mixture in the temperature range from 20° to 170° C. for 1 to 7 hours. A further solvent is not necessary for the reaction. The reaction is normally carried out under anhydrous conditions when using dialkyl alkanephosphonate as alkylating reagent. After conventional working up, the product of formula (1) is obtained in good yield and high purity.

The invention also relates to a process for the preparation of bis(hydroxyphenyl)-1,3,5-triazines of formula (2). The process comprises reacting a benzonitrile of formula (I) with a benzonitrile of formula (II) in the temperature range from 180° to 260° C., in which formulae $R_1$ and $R_2$ have the given meanings, to the compound of formula (2).

By means of this process it is possible to prepare bis(hydroxyphenyl)-1,3,5-triazines in simple manner and in good yield.

The triazines obtained by the inventive process find utility as UV absorbers or as starting materials for the preparation of UV absorbers.

The invention is illustrated by the following Examples.

EXAMPLE 1

35.2 g (0.3 mol) of p-tolunitrile and 11.9 g (0.1 mol) of 2-hydroxybenzonitrile are brought together in the reactor and, with stirring, the mixture is heated to 217° C. The clear reddish melt is stirred for 6 hours at 217°–222° C. The melt is then cooled to 80° C. and diluted with 20 ml of ethanol. The readily stirrable suspension so obtained is cooled to room temperature and filtered. The filter product is washed with several portions of ethanol and water and vacuum dried at 80° C., affording 10.5 g of a bright powder of formula

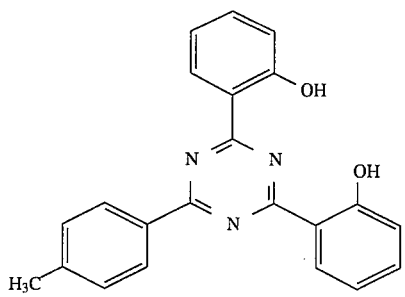
(101)

corresponding to a yield of 59.2% of theory. Melting point: 258°–259° C.

The product still contains a minor amount of tris(o-hydroxyphenyl)-1,3,5-triazine (compound of formula (103) as impurity. The melting point of the recrystallised product is 258°–259° C.

EXAMPLE 2

The procedure as described in Example 1 is repeated, but reacting 93.6 g (0.8 mol) of p-tolunitrile and 119 g (1 mol) of 2-hydroxybenzonitrile for 15 hours at 210°–217° C., affording 138.5 g of the compound of formula (101), corresponding to a yield of 77.9 % of theory.

EXAMPLE 3

The procedure as described in Example 1 is repeated, but using 20.6 g (0.2 mol) of benzonitrile instead of 35.2 g of tolunitrile. After a reaction time of 6 hours at 190° to 195° C., there are obtained 10.4 g of a mixture of the compound of formula

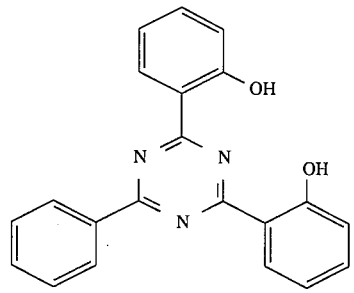
(102)

and

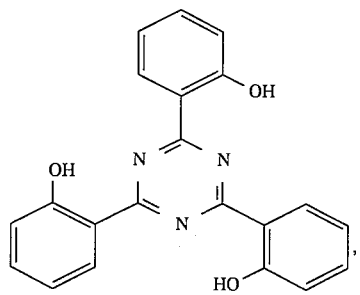
(103)

which mixture consists mainly of the compound of formula (102), corresponding to a yield of 60.9% of theory.

EXAMPLE 4

The procedure as described in Example 3 is repeated, but using 35.7 g (0.3 mol) of 2-hydroxybenzonitrile and 30.9 g (0.3 mol) of benzonitrile. After a reaction time of 6 hours at 250° C. in a steel autoclave, working up gives 41.9 g of a product that consists mainly of the compound of formula (102), corresponding to a yield of 81.8% of theory.

EXAMPLE 5

The procedure as described in Example 1 is repeated, but using 79.9 g (0.6 mol) of 4-methoxybenzonitrile (instead of 35.2 g of p-tolunitrile) and 23.8 g (0.2 mol) (instead of 11.9 g) of 2-hydroxybenzonitrile. After a reaction time of 8 hours in the temperature range from 245° to 260° C., working up gives 14.9 g (40.1% of theory) of the compound of formula

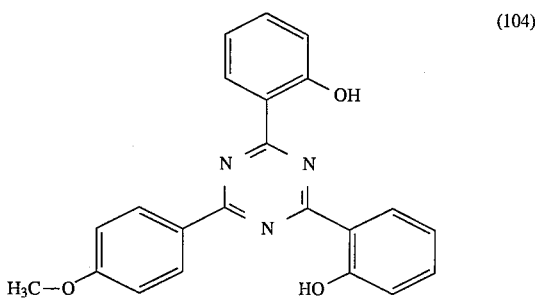
(104)

EXAMPLE 6

The compound of formula (101) is converted with dimethyl methanephosphonate and sodium carbonate as base at 150° C. and after a reaction time of 4 hours into the compound of formula

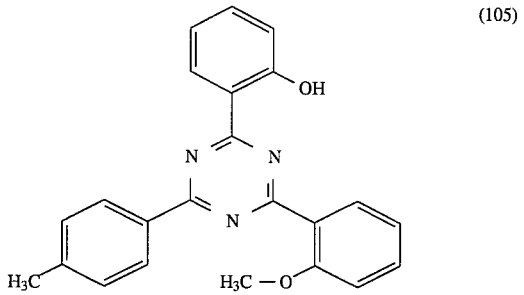
(105)

Melting point: 168°–169° C.

EXAMPLE 7

As described in Example 6, the compound of formula (102) is converted into the compound of formula

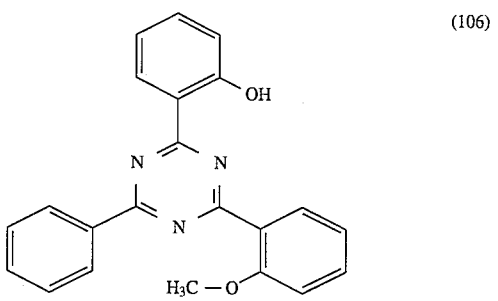
(106)

Melting point: 153°–155° C.

EXAMPLE 8

As described in Example 6, the compound of formula (104) is converted into the compound of formula

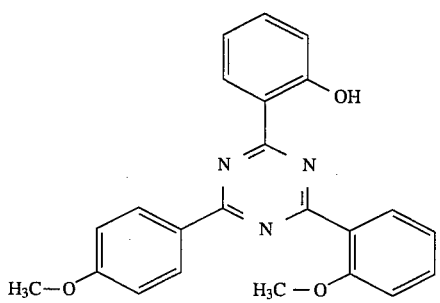
(107)

Melting point: 152°–153° C.

What is claimed is:

1. A process for the preparation of a triazine of formula

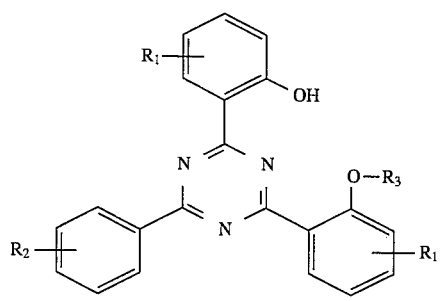
(1)

which comprises, in a first reaction step, reacting a benzonitrile of formula (I)

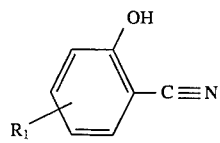

with a nitrile of formula (II)

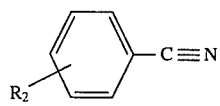

to the compound of formula

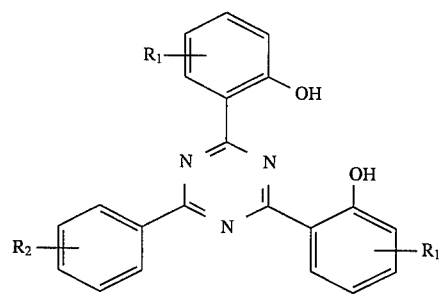
(2)

and, in a second reaction step, reacting said compound by selective alkylation to the compound of formula (1), in which formulae above $R_1$ and $R_2$ are each independently of the other hydrogen, halogen, —C≡N, $C_1$–$C_{18}$alkyl or $C_1$–$C_{18}$alkoxy and $R_3$ is $C_1$–$C_{18}$alkyl.

2. A process according to claim 1, wherein the alkylating reagent is a dialkyl alkanephosphonate or dialkyl sulfate.

3. A process according to claim 1 wherein the alkylating reagent is dimethyl alkanephosphonate or dimethyl sulfate.

4. A process according to claim 1, wherein the reaction of the second step is carried out in the temperature range from 180° to 260° C.

5. A process according to claim 1, wherein the molar ratio of the benzonitriles of formulae (I) and (II) is 2:1 to 1:10.

6. A process according to claim 4 for the preparation of a compound of formula (1), wherein $R_1$ and $R_2$ are each hydrogen, and $R_3$ is $C_1$–$C_{18}$alkoxy.

7. A process according to claim 1, wherein the reaction time for the first reaction step is from 2 to 24 hours, preferably from 5 to 12 hours.

8. A process according to claim 1, wherein the reaction in the first reaction step is carried out without a solvent.

9. A process according to claim 1, wherein the reaction in the first reaction step is carried out without the use of a catalyst.

10. A process for the preparation of a triazine of formula

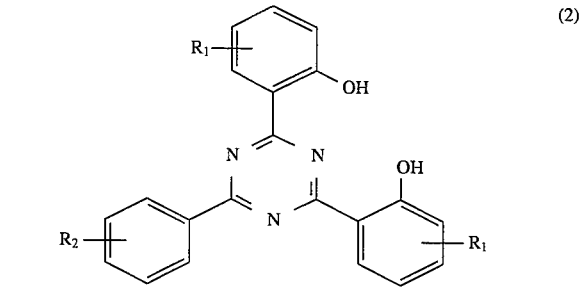
(2)

which comprises reacting a benzonitrile of formula (I)

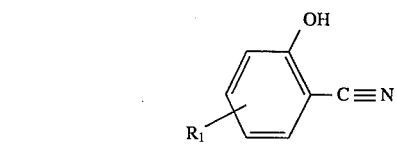

with a benzonitrile of formula (II)

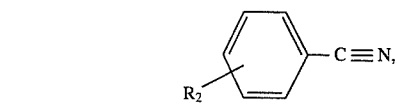

in the temperature range from 180° to 260° C., in which formulae above $R_1$ and $R_2$ are each independently of the other hydrogen, halogen, —C≡N, $C_1$–$C_{18}$alkyl or $C_1$–$C_{18}$alkoxy.

* * * * *